(12) United States Patent
Kikuchi

(10) Patent No.: US 7,905,727 B2
(45) Date of Patent: Mar. 15, 2011

(54) IMPLANT KEEPER AND ITS ASSEMBLY, AND KEEPER-FIXING METHOD

(75) Inventor: Akira Kikuchi, Oosato-gun (JP)

(73) Assignee: Hitachi Metals, Ltd., Tokyo (JP)

( * ) Notice: Subject to any disclaimer, the term of this patent is extended or adjusted under 35 U.S.C. 154(b) by 338 days.

(21) Appl. No.: 12/261,633

(22) Filed: Oct. 30, 2008

(65) Prior Publication Data

US 2009/0117520 A1  May 7, 2009

(30) Foreign Application Priority Data

Nov. 1, 2007  (JP) ................................. 2007-284735

(51) Int. Cl.
*A61C 13/235* (2006.01)
*A61C 8/00* (2006.01)

(52) U.S. Cl. .......................... 433/189; 433/172; 433/174

(58) Field of Classification Search .................... 433/60, 433/172–176, 189; 403/305–307
See application file for complete search history.

(56) References Cited

U.S. PATENT DOCUMENTS

| | | | | |
|---|---|---|---|---|
| 4,722,688 A | * | 2/1988 | Lonca | 433/173 |
| 4,790,753 A | * | 12/1988 | Fradera | 433/174 |
| 4,842,518 A | * | 6/1989 | Linkow et al. | 433/174 |
| 4,993,950 A | * | 2/1991 | Mensor, Jr. | 433/173 |
| 5,421,722 A | * | 6/1995 | Stemmann | 433/189 |
| 5,658,146 A | * | 8/1997 | Kisielewski et al. | 433/172 |
| 5,863,200 A | * | 1/1999 | Hamada et al. | 433/173 |
| 6,174,166 B1 | * | 1/2001 | Jorneus | 433/172 |
| RE37,646 E | * | 4/2002 | Zuest | 433/173 |
| 6,709,270 B2 | | 3/2004 | Honkura et al. | |
| 2007/0020583 A1 | * | 1/2007 | Kojima | 433/173 |

FOREIGN PATENT DOCUMENTS

| | | |
|---|---|---|
| EP | 0 323 421 A2 | 7/1989 |
| JP | 01-190350 A | 7/1989 |
| JP | 2000-279428 A | 10/2000 |
| JP | 2003-250816 | 9/2003 |

* cited by examiner

*Primary Examiner* — John J Wilson
(74) *Attorney, Agent, or Firm* — Sughrue Mion, PLLC

(57) ABSTRACT

A keeper for an implant comprising a keeper body made of a soft-magnetic material, which has a recess for receiving an abutment head having an internally threaded hole, and an internally threaded hole extending along its center axis in communication with the recess, and a screw member threadably engageable with the internally threaded holes of the keeper body and the abutment, whereby the keeper body is tightly fastened to the abutment by tension exerted by the screw member threadably engaging the internally threaded holes of the keeper body and the abutment.

9 Claims, 5 Drawing Sheets

IMPLANT KEEPER AND ITS ASSEMBLY, AND KEEPER-FIXING METHOD

CROSS REFERENCE TO RELATED APPLICATION

This application claims priority based on Japanese Patent Application No. 2007-284735, filed Nov. 1, 2007, the contents of which are incorporated herein by reference in their entirety.

FIELD OF THE INVENTION

The present invention relates to a keeper for an implant for fixing a magnetic attachment for a denture to an implant body, and its assembly, and a method for fixing such a keeper.

BACKGROUND OF THE INVENTION

To make a denture easily detachable in dental implanting, a method of fixing a soft-magnetic keeper to an implant body embedded in the jawbone, and causing a magnet-containing denture attachment to be magnetically attracted to the keeper has recently become widely used.

U.S. Pat. No. 6,709,270 discloses a magnet-containing denture attachment magnetically attached to a keeper made of a soft-magnetic material and threadably engaging an implant body. The keeper comprises a frustoconical portion, and a ring portion extending from an upper peripheral of the frustoconical portion and provided with an annular groove to have a lower end portion having a gradually reducing thickness. The implant body comprises a conical recess complementary to the frustoconical portion of the keeper. When the keeper is screwed into the implant body, the lower end portion of the ring portion abutting the implant body is elastically deformed, generating tension by which the keeper is prevented from slackening. However, because there is a small contact area between the lower end portion of the ring portion and the implant body, plastic deformation occurs in the lower end portion of the ring portion by a long period of use, resulting in decreased tension and thus slackening the keeper.

In the implanting of front teeth to the upper jaw, etc., an abutment with an angled head is used to make a slanting denture. For instance, EP 0323421 A discloses a dental implant, in which an angled spacer is attached to an implant body embedded in the jawbone, and a dental bridge is fixed to a spacer head with a bolt. However, because the dental bridge to be fixed to the angled spacer with a screw does not have a female thread, the dental bridge is not firmly fastened to the angled spacer, resulting in slackening by a long period of use.

OBJECTS OF THE INVENTION

Accordingly, an object of the present invention is to provide a keeper for an implant easily fixed to an abutment without slackening between the keeper and the abutment even after a long period of use.

Another object of the present invention is to provide a keeper assembly for an implant comprising the above implant keeper and an abutment.

A further object of the present invention is to provide a method for fixing the above keeper to an abutment.

DISCLOSURE OF THE INVENTION

The keeper for an implant (simply called "implant keeper") of the present invention comprises a keeper body made of a soft-magnetic material, which has a recess for receiving an abutment head having an internally threaded hole, and an internally threaded hole extending along its center axis in communication with the recess, and a screw member threadably engageable with the internally threaded holes of the keeper body and the abutment, whereby the keeper body is tightly fastened to the abutment by tension exerted by the screw member threadably engaging the internally threaded holes of the keeper body and the abutment.

It is preferable that the abutment has a frustoconical head, and that the recess of the keeper body has a conical inner surface complementary to the head of the abutment. The keeper body preferably has a nut-shaped head.

The method of the present invention for fixing a keeper body made of a soft-magnetic material to an abutment comprising a head having an internally threaded hole with a screw member, the keeper body having a recess for receiving the abutment head, a nut-shaped head, and an internally threaded hole extending along its center axis in communication with the recess, comprises the steps of capping the head of the abutment with the keeper body; screwing the screw member into the internally threaded holes of the keeper body and the abutment; and then rotating the keeper body in a screwing direction with a tool engaging the nut-shaped head, until the keeper body is tightly fastened to the abutment.

The keeper assembly for an implant (simply called "implant keeper assembly") of the present invention assembly to be fixed to an implant body embedded in the bone, comprises (a) an abutment comprising a slanting head and an internally threaded hole extending along its center axis, and fixed to the implant body; and (b) a keeper comprising a keeper body made of a soft-magnetic material, which comprises a recess for receiving the head of the abutment, a nut-shaped head, and an internally threaded hole extending along its center axis in communication with the recess, and a screw member threadably engageable with the internally threaded holes of the keeper body and the abutment; said keeper body being tightly fastened to said abutment by a tool engaging said nut-shaped head with said screw member threadably engaging the internally threaded holes of said keeper body and said abutment.

In the implant keeper and its assembly of the present invention, after the screw member is screwed into the internally threaded holes of the keeper body and the abutment, the keeper body is preferably rotated in a screwing direction until the keeper body is tightly fastened to the abutment.

It is preferable that the abutment comprises a cylindrical portion inserted into a center hole of the implant body, and a through-hole extending from the head to the cylindrical portion, which is open at the side surface of the head, a screw for fixing the abutment to the implant body being inserted into the through-hole.

DESCRIPTION OF THE BEST MODE OF THE INVENTION

[1] Keeper Assembly for an Implant

Figure 1:
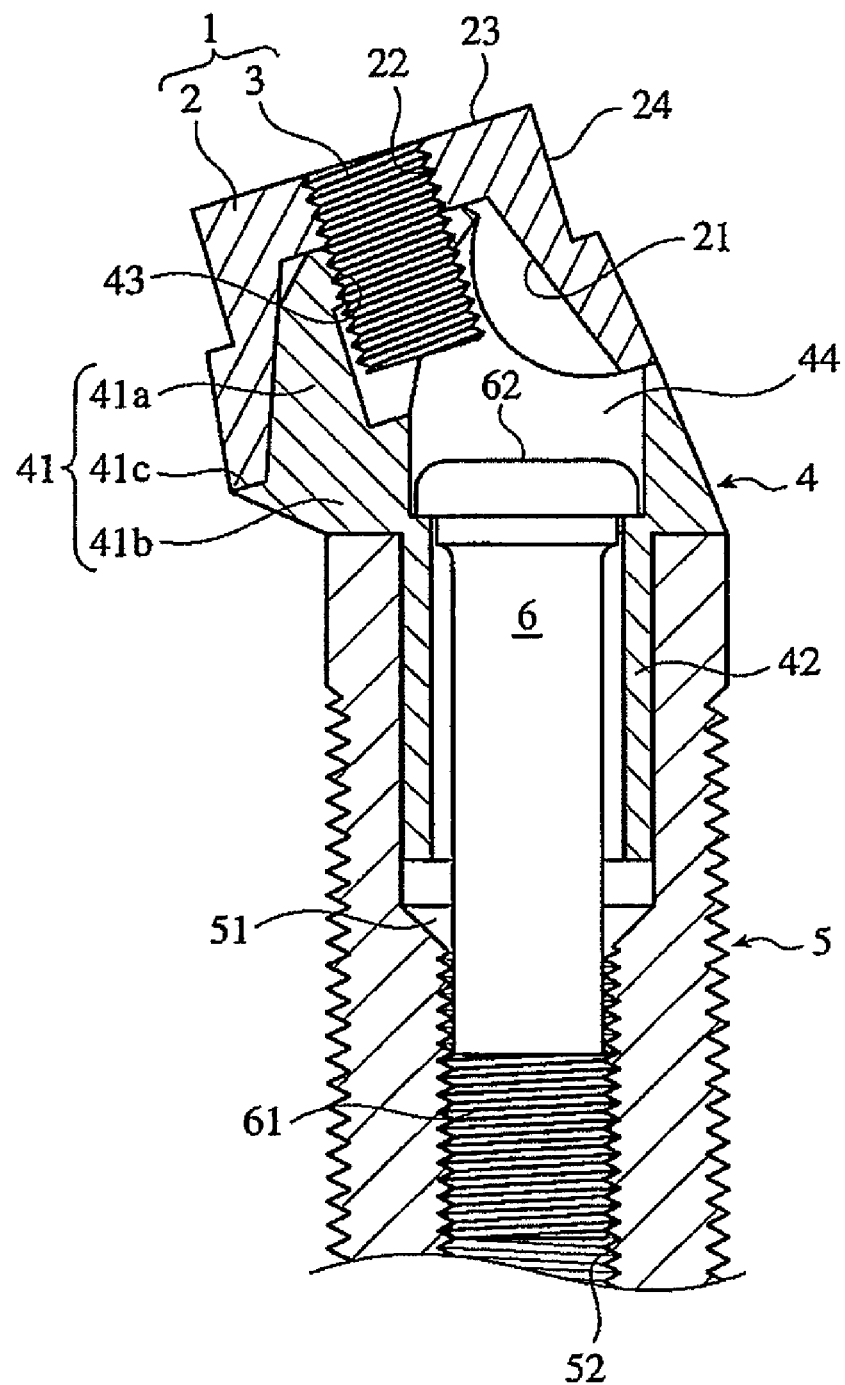
FIG. 1 is a cross-sectional view showing an implant keeper according to one embodiment of the present invention, which is fixed to an abutment.
Figure 2:
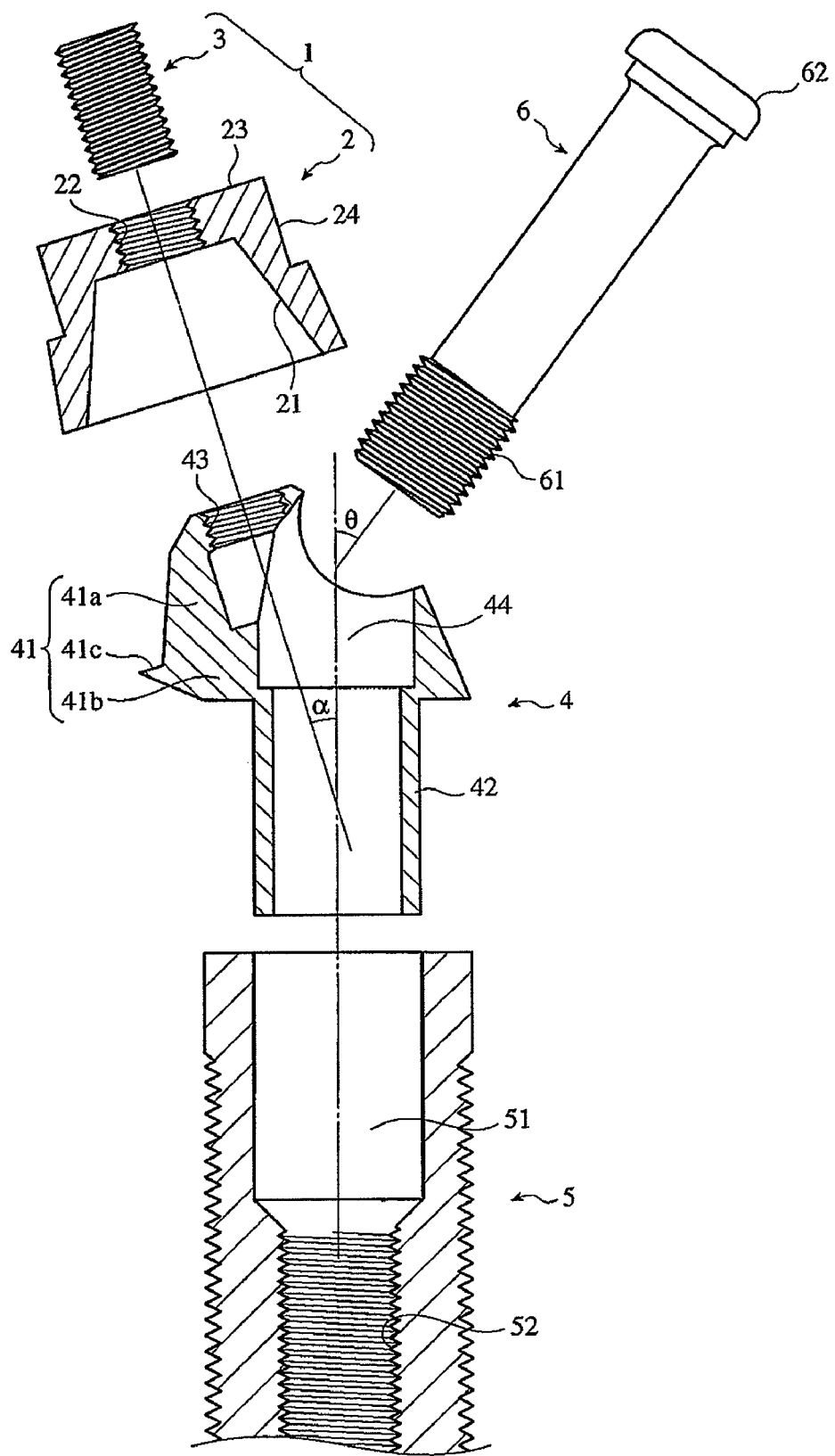
FIG. 2 is an exploded view showing the implant keeper of FIG. 1, which is fixed to an abutment.

The implant keeper assembly according to one embodiment of the present invention, which is shown in FIGS. 1 and 2, comprises an abutment 4 to be fixed to an implant body 5, and an implant keeper 1 comprising a keeper body 2 fastened to a head 41 of the abutment 4 and a screw member 3 such as a set screw. The implant body 5 is a cylindrical member having a male thread on the outer surface, which is embedded in the jawbone. The implant body 5 comprises a center hole 51 into which a cylindrical portion 42 extending downward from the head 41 of the abutment 4 and a bolt 6 are inserted, and an internally threaded hole 52 provided on the deeper side of the center hole 51 for threadably engaging a male-threaded tip portion 61 of the bolt 6. The implant body 5 preferably has an outer diameter of 3-6.5 mm and a length of about 10 mm for usual implanting.

The abutment 4 comprises a head 41 engageable with the keeper 1, and a cylindrical portion 42 in which the bolt 6 is inserted. The head 41 comprises a frustoconical portion 41a complementary to a recess 21 of the keeper body 2, and a base portion 41b brought into contact with an upper end of the implant body 5, and the base portion 41b has a flange 41c extending from a lower end of the frustoconical portion 41a. The frustoconical portion 41a has an internally threaded center hole 43 which is open at the upper end, and a screw member 3 of the keeper 1 threadably engages the internally threaded hole 43. A through-hole 44 coaxially extending from the cylindrical portion 42 is open on the side surface of the head 41, with its direction changed by an angle $\theta$ in the head 41. The frustoconical portion 41a of the abutment 4 is slanting by an angle $\alpha$ from the cylindrical portion 42 (through-hole 44). The angle $\alpha$ is in a range of usually 15-35°, preferably 15-30°.

After the cylindrical portion 42 of the abutment 4 is inserted into the center hole 51 of the implant body 5, the bolt 6 is inserted into the through-hole 44 of the abutment 4, and the male-threaded portion 61 of the bolt 6 is screwed into the internally threaded hole 52 of the implant body 5 to fix the abutment 4 to the implant body 5.

From the aspect of the biocompatibility with the jawbone, corrosion resistance and mechanical strength, the implant body 5 is preferably made of pure titanium, titanium alloys, etc. To have improved biocompatibility, the implant body 5 may be surface-treated with hydroxyapatite. The abutment 4 is preferably made of the same material as that of the implant body 5.

As shown in FIGS. 2-8, the implant keeper 1 according to one embodiment of the present invention comprises a keeper body 2 comprising a conical recess 21 complementary to the frustoconical portion 41a of the head 41 of the abutment 4, and an internally threaded hole 22 communicating with the recess 21 and open at a center of the upper surface 23, and a screw member 3 threadably engaging the internally threaded hole 22 of the keeper body 2 and the internally threaded hole 43 of the abutment 4. Referring to FIGS. 3-6, the keeper body 2 having a height t1 has an outer shape obtained by machining an upper portion of a frustum (D1<D2) to a regular-hexagonal nut shape when viewed from above. A nut-shaped head having a height t3, which is about ½ of t1, has six nut-constituting surfaces, an upper peripheral edge comprising upper straight lines of the nut-constituting surfaces and upper circular lines (outer diameter D1) of the frustum, and six triangular frustoconical surfaces 20 remaining between adjacent nut-constituting surfaces. The nut-shaped head has a size adapted to the hexagon nut standard (JIS B 1181). The size of the upper surface 23 of the keeper body 2 is properly determined depending on a denture attachment (see FIG. 9). The recess 21 of the keeper body 2 preferably has a conical inner surface complementary to the frustoconical portion 41a of the head 41 of the abutment 4.

The screw member 3 for connecting the keeper body 2 to the abutment 4 comprises a flat head having a slot 32 engageable with a tool such as a minus driver, and has a normal diameter of 1-2 mm (M1-M2). The screw member 3 has such a length L that it has a portion of length $L_1$ threadably engageable with the internally threaded hole 22 of the keeper body 2, and a portion of length $L_2$ threadably engageable with the internally threaded hole 43 of the abutment 4, as well as a portion of length $L_3$ extending without interference into a hollow recess of the abutment 4 communicating with the through-hole 44 (see FIGS. 8 and 9).

Because the keeper body 2 should be made of a soft-magnetic material for magnetic attraction to a denture attachment, it is preferably made of ferrite-type, stainless steel (according to JIS G 4303) having excellent soft-magnetic properties and corrosion resistance. Although the screw member 3 is preferably made of a soft-magnetic material like the keeper body 2 such that its upper surface is magnetically attracted to the denture attachment, the screw member 3 may be made of a non-magnetic material such as a titanium alloy because it is small. Each of the male thread of the screw member 3 and the internally threaded holes of the keeper body 2 and the abutment 4 preferably has a nominal diameter of 1-3 mm.

[2] Method for Fixing Implant Keeper to Abutment

The cylindrical portion 42 of the abutment 4 is inserted into the center hole 51 of the implant body 5 embedded in the jawbone, and the bolt 6 penetrating the through-hole 44 of the abutment 4 is threadably engaged with the internally threaded hole 52 of the implant body 5 to fix the abutment 4 to the implant body 5. After the abutment 4 is capped with the keeper body 2, the screw member 3 is screwed into the internally threaded hole 22 of the keeper body 2 and the internally threaded hole 43 of the abutment 4 with a tool such as a minus driver. In this case, an upper end of the screw member 3 should not project from the upper surface of the keeper body 2. For instance, the upper end of the screw member 3 is substantially on the same plane as the upper surface of the keeper body 2. When the keeper body 2 is rotated in a screwing direction (usually direction of a right-hand thread) with a torque wrench of a predetermined torque (for instance, 20-30 N·cm) in a state where the keeper body 2 is in contact with the abutment 4, the screw member 3 is subjected to tension from the keeper body 2 and the abutment 4. This is tantamount to a state that the keeper body 2 and the abutment 4 are pulled by the screw member 3, so that the keeper body 2 is firmly fastened to the abutment 4. As a result, the keeper 1 does not slacken even under repeated load.

[3] Magnetic Attachment

Figure 9:
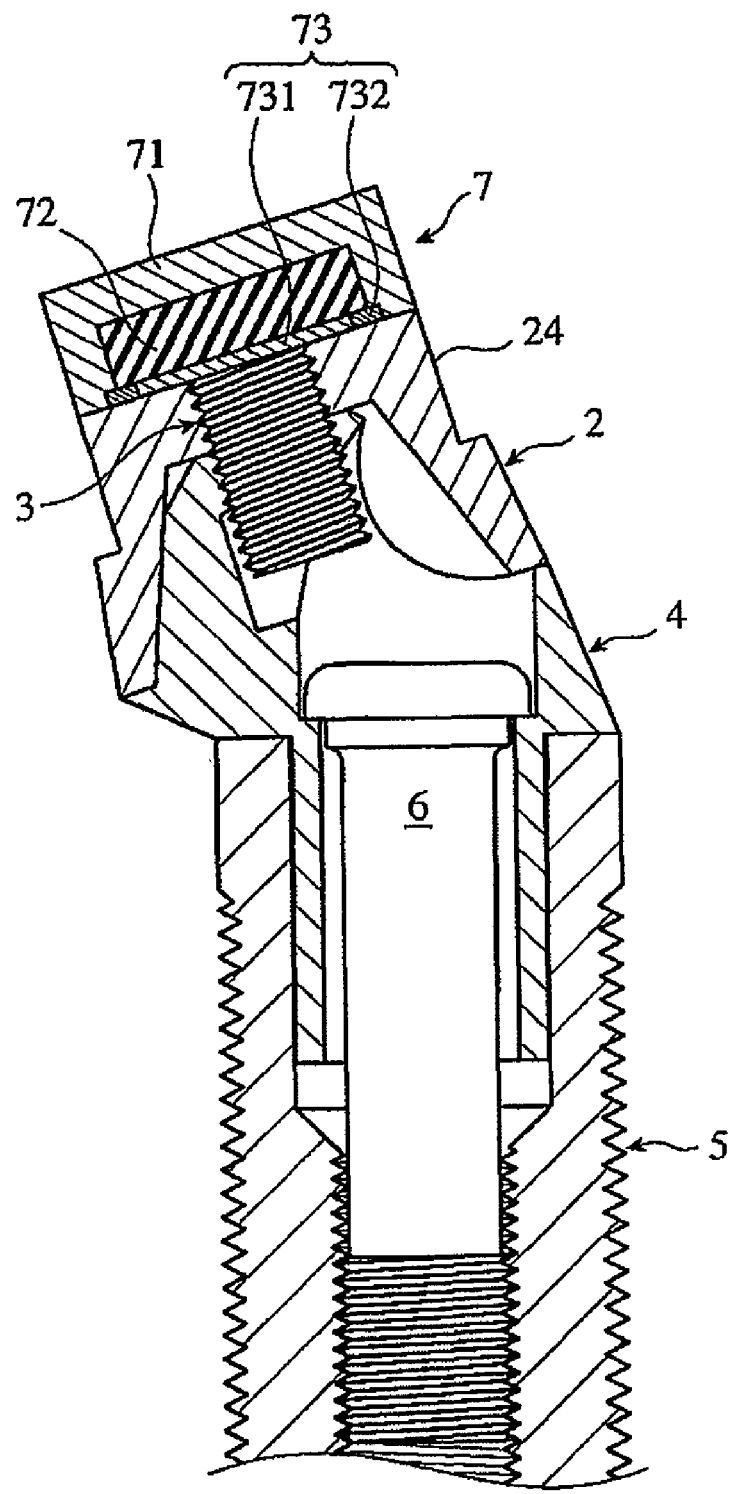
FIG. 9 is a front view showing the keeper of FIG. 1 for an implant, which is attracted to an attachment.

As shown in FIG. 9, a magnetic attachment 7 of a denture is magnetically attracted to the upper surface 23 of the keeper body 2 of the present invention, to fix the denture. The magnetic attachment 7 per se may be a known one (see WO 2005/077297). The magnetic attachment 7 shown in FIG. 9 comprises a cup-shaped yoke 71 having a circular-cross-sectioned recess and made of a soft-magnetic material, a disc-shaped, permanent magnet 72 received in the recess and magnetized in a thickness direction, and a seal plate 73 fit in the opening of the recess. The seal plate 73, a member for sealing the permanent magnet 72 in the recess and forming a magnetic path, is constituted by a disc-shaped yoke 731 made of a soft-magnetic material, and a seal ring 732 made of a non-magnetic material and welded to the periphery of the disc-shaped yoke 731. The above soft-magnetic material is preferably a corrosion-resistant metal such as ferrite stainless steel (for instance, SUS447J1), and the above non-magnetic material is preferably a corrosion-resistant metal such as austenitic stainless steel (for instance, SUS316L).

The permanent magnet 72 is preferably made of a sintered R-T-B magnet such as an anisotropic, sintered Nd—Fe—B magnet having high magnetic properties, which preferably has a composition comprising 27-34% by mass of R (at least one of rare earth elements including Y with at least one of Nd, Dy and Pr indispensable), and 0.6-1.8% by mass of B, the balance being substantially T (Fe or Co). Less than 27% by mass of R provides the magnet with too low coercivity (iHc), and more than 34% by mass of R extremely reduces the residual magnetic flux density Br of the magnet. Less than 0.6% by mass of B fails to provide the magnet with practically useful coercivity, and more than 1.8% by mass of B extremely reduces the Br. The more preferred composition of the sintered R-T-B magnet comprises 27-32% by mass of R, 0.6-1.8% by mass of B, 0.0001-20% by mass of Co, and 0.001-3% by mass of M (at least one selected from the group consisting of Al, Si, Cu, Ga, Nb, Mo and W), the balance being substantially Fe.

The present invention will be described in detail with reference to Examples below without intension of limitation.

Example 1

Figure 3:
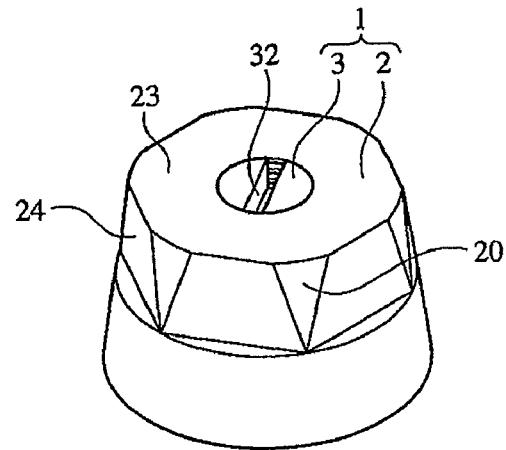
FIG. 3 is a perspective view showing an implant keeper according to one embodiment of the present invention.
Figure 4:
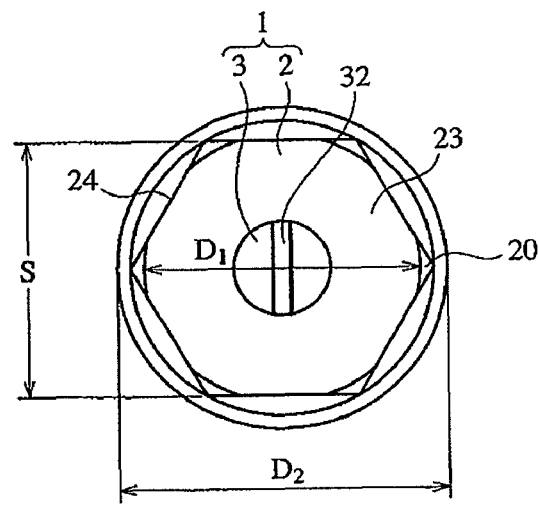
FIG. 4 is a plan view showing the keeper of FIG. 3 for an implant.
Figure 5:
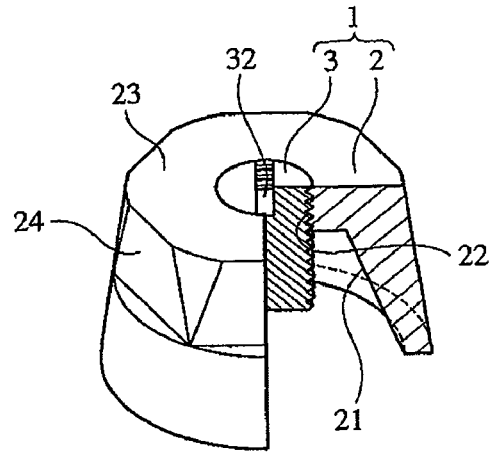
FIG. 5 is a partially cross-sectional, perspective view showing the keeper of FIG. 3 for an implant.
Figure 6:
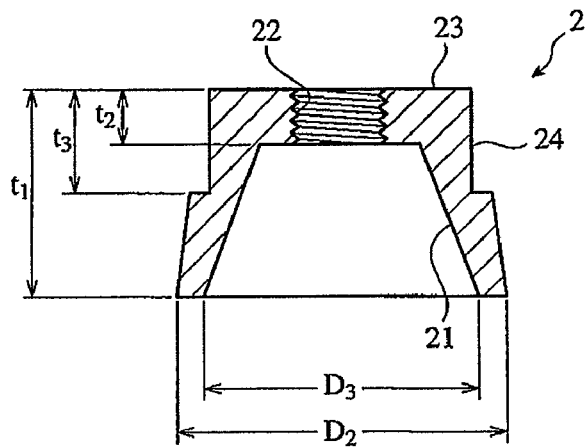
FIG. 6 is a partially cross-sectional, front view showing a keeper body in the keeper of FIG. 3 for an implant.
Figure 7:
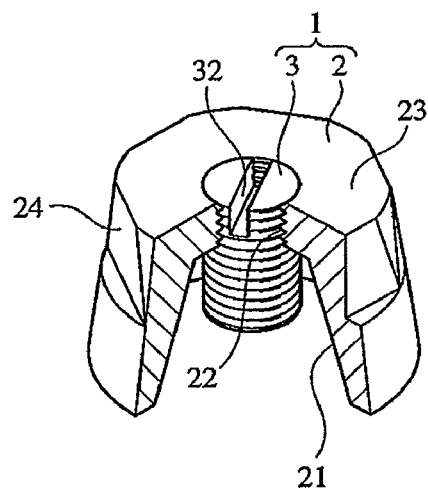
FIG. 7 is a partially cross-sectional, perspective view showing the keeper of FIG. 3 for an implant.
Figure 8:
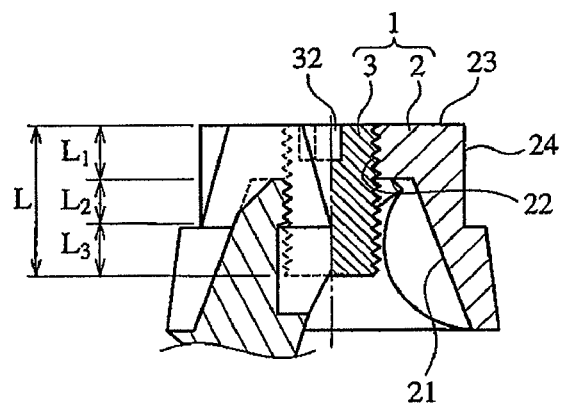
FIG. 8 is a partially cross-sectional, front view showing the keeper of FIG. 3 for an implant.

As shown in FIGS. 3, 4 and 6, a keeper body 2 having a nut-shaped head having S of 3.9 mm (standard dimensions of hexagon M2 nuts: 4-3.82 mm), D1 of 4.0 mm and t3 of 1.5 mm, t1 of 3.0 mm, t2 of 0.8 mm, D2 of 4.8 mm, D3 of 4.0 mm, and a nominal diameter of the internally threaded hole of 1.4 mm (corresponding to M1.4) was formed by ferrite stainless steel (SUSXM27). Also, a screw member 3 having a normal diameter of 1.4 mm and a length of 2.2 mm was formed by a titanium alloy (Ti-6Al-4V). As shown in FIG. 1, after an abutment 4 fixed to an implant body 5 made of a titanium alloy (Ti-6Al-4V) was capped with a keeper body 2, a screw member 3 was screwed into an internally threaded hole 22 of the keeper body 2 and an internally threaded hole 43 of the abutment 4 with a minus driver. An upper end of the screw member 3 did not project from an upper surface of the keeper body 2. The keeper body 2 was rotated in a screwing direction with a torque wrench set to provide a torque of 30 N·cm. The keeper 1 did not slacken even after applying a load of 200 N $1 \times 10^6$ times vertically to the upper surface 23 of the keeper body 2.

EFFECT OF THE INVENTION

When the keeper body made of a soft-magnetic material is attached to the abutment head with a screw member, and then rotated in a screwing direction until it is fastened to the abutment head, the keeper body and the abutment are pulled by the screw member. As a result, the keeper body is firmly fastened to the abutment. Therefore, the keeper body does not slacken even after a long period of use. Because the implant keeper of the present invention comprises small number of parts and is easily attached to the abutment, it enables dental implanting in a short period of time.

What is claimed is:

1. A keeper for an implant comprising a keeper body made of a soft-magnetic material, which has a recess for receiving an abutment head having an internally threaded hole, and an internally threaded hole extending along its center axis in communication with said recess, and a screw member threadably engageable with the internally threaded holes of said keeper body and said abutment, whereby said keeper body is tightly fastened to said abutment by tension exerted by said screw member threadably engaging the internally threaded holes of said keeper body and said abutment.

2. The keeper for an implant according to claim 1, wherein after said screw member is screwed into the internally threaded holes of said keeper body and said abutment, said keeper body is rotated in a screwing direction until said keeper body is tightly fastened to said abutment.

3. The keeper for an implant according to claim 1, wherein said abutment has a frustoconical head, and the recess of said keeper body has a conical inner surface complementary to the head of said abutment.

4. The keeper for an implant according to claim 1, wherein said keeper body has a nut-shaped head.

5. A method for fixing a keeper body made of a soft-magnetic material to an abutment comprising a head having an internally threaded hole with a screw member, said keeper body having a recess for receiving the abutment head, a nut-shaped head, and an internally threaded hole extending along its center axis in communication with said recess, comprising the steps of capping the head of said abutment with said keeper body; screwing said screw member into the internally threaded holes of said keeper body and said abutment; and then rotating said keeper body in a screwing direction with a tool engaging said nut-shaped head, until said keeper body is tightly fastened to said abutment.

6. A keeper assembly for an implant to be fixed to an implant body embedded in the bone, comprising (a) an abutment comprising a slanting head and an internally threaded hole extending along its center axis, and fixed to said implant body; and (b) a keeper comprising a keeper body made of a soft-magnetic material, which has a recess for receiving the head of said abutment, a nut-shaped head, and an internally threaded hole extending along its center axis in communication with said recess, and a screw member threadably engageable with the internally threaded holes of said keeper body and said abutment; said keeper body being tightly fastened to said abutment by a tool engaging said nut-shaped head with said screw member threadably engaging the internally threaded holes of said keeper body and said abutment.

7. The keeper assembly for an implant according to claim 6, wherein after said screw member is screwed into the internally threaded holes of said keeper body and said abutment, said keeper body is rotated in a screwing direction until said keeper body is tightly fastened to said abutment.

8. The keeper assembly for an implant according to claim 6, wherein said abutment has a frustoconical head, and the recess of said keeper body has a conical inner surface complementary to the head of said abutment.

9. The keeper assembly for an implant according to claim 6, wherein said abutment comprises a cylindrical portion inserted into a center hole of said implant body, and a through-hole extending from said head to said cylindrical portion, which is open at the side surface of said head, a screw for fixing said abutment to said implant body being inserted into said through-hole.

* * * * *